US011304821B2

(12) United States Patent
Berry (10) Patent No.: US 11,304,821 B2
(45) Date of Patent: Apr. 19, 2022

(54) DUAL EXPANDABLE SPINAL IMPLANT

(71) Applicant: Bret Michael Berry, Tallahassee, FL (US)

(72) Inventor: Bret Michael Berry, Tallahassee, FL (US)

( * ) Notice: Subject to any disclaimer, the term of this patent is extended or adjusted under 35 U.S.C. 154(b) by 198 days.

(21) Appl. No.: 16/600,134

(22) Filed: Oct. 11, 2019

(65) Prior Publication Data

US 2020/0352731 A1 Nov. 12, 2020

Related U.S. Application Data

(63) Continuation-in-part of application No. 16/409,149, filed on May 10, 2019, now Pat. No. 10,881,531.

(51) Int. Cl.
*A61F 2/44* (2006.01)
*A61F 2/30* (2006.01)
*A61F 2/28* (2006.01)

(52) U.S. Cl.
CPC ...... *A61F 2/447* (2013.01); *A61F 2002/2835* (2013.01); *A61F 2002/30266* (2013.01);
(Continued)

(58) Field of Classification Search
CPC ...... A61F 2/447; A61F 2/4455; A61F 2/4611; A61F 2/4425; A61F 2002/2835; A61F 2002/30266; A61F 2002/30387; A61F 2002/30398; A61F 2002/30405; A61F 2002/30528; A61F 2002/30579;
(Continued)

(56) References Cited

U.S. PATENT DOCUMENTS 9,566,168 B2 * 2/2017 Glerum ................. A61F 2/4425
10,507,116 B2 * 12/2019 Shoshtaev ............. A61F 2/4455
(Continued)

FOREIGN PATENT DOCUMENTS

DE 102018206693 B3 2/2019

OTHER PUBLICATIONS

International Search Report and Written Opinion for PCT Patent Application No. PCT/US20/55042, dated Jan. 21, 2021.

*Primary Examiner* — Pedro Philogene
(74) *Attorney, Agent, or Firm* — Ellenoff Grossman & Schole LLP; James M. Smedley; Alex Korona (57) ABSTRACT

Apparatus and associated methods relate to a spinal implant configured to expand both vertically and laterally at the same time when wedges coupled by a threaded post drive movable spinal implant endplates radially outward from the longitudinal axis of the threaded post, displacing the wedges and expanding the implant as the threaded post turns. In an illustrative example, the wedges may be a pair of wedges configured with dual inclined planes. The inclined planes may be, for example, disposed both vertically and laterally with respect to the threaded post longitudinal axis, permitting implant expansion both vertically and laterally simultaneously. In some examples, the wedges may be cones. Some embodiments may include an aligning support. In some samples, the aligning support is a pair of rails adapted to prevent rotation of the wedges. Various examples may advantageously provide improved stability and reduced subsidence, based on increased vertebral body contact area with an implant expanded in place to the desired height and width.

19 Claims, 7 Drawing Sheets

(52) U.S. Cl.
CPC ........... *A61F 2002/30387* (2013.01); *A61F 2002/30398* (2013.01); *A61F 2002/30405* (2013.01); *A61F 2002/30528* (2013.01); *A61F 2002/30579* (2013.01)

(58) Field of Classification Search
CPC .. A61F 2002/30156; A61F 2002/30471; A61F 2002/30411; A61F 2002/30904; A61F 2002/443; A61F 2002/30518; A61F 2002/30176; A61F 2002/30593; A61F 2002/30331; A61F 2002/3055; A61F 2002/30624; A61F 2002/30476; A61F 2002/30482; A61F 2002/30537
See application file for complete search history.

(56) References Cited

U.S. PATENT DOCUMENTS

| | | |
|---|---|---|
| 2011/0319997 A1* | 12/2011 | Glerum .................. A61F 2/442 623/17.15 |
| 2014/0039622 A1 | 2/2014 | Glerum et al. |
| 2018/0193164 A1 | 7/2018 | Shoshtaev |
| 2019/0269521 A1 | 9/2019 | Shoshtaev |
| 2019/0388232 A1 | 12/2019 | Purcell et al. |
| 2020/0352731 A1 | 11/2020 | Berry |

* cited by examiner

DUAL EXPANDABLE SPINAL IMPLANT

CROSS-REFERENCE TO RELATED APPLICATIONS

This application claims the benefit of U.S. Nonprovisional patent application Ser. No. 16/409,149 entitled DUAL EXPANDABLE SPINAL IMPLANT filed on May 10, 2019 which is hereby incorporated by reference in its entirety.

TECHNICAL FIELD

Various embodiments relate generally to spinal implants.

BACKGROUND

Spinal implants are medical devices used to treat problems with a patient's spine. A surgeon may install a spinal implant in a patient's spine during spinal surgery. In some examples, a patient may have spinal implant surgery to stabilize the spine, or relieve pain. For example, a patient may suffer from back pain due to spinal damage or deterioration, which may result in spinal instability. In an illustrative example, spinal instability may be a result of injury, or disease.

Some spinal conditions may be treated with surgical removal of a disc or associated tissues, however, when the disc nucleus is removed without subsequent stabilization, the same disabling back pain may reoccur due to persistent inflammation, or instability. In some scenarios, adjacent vertebrae may be fused together through a fusion device implanted between the vertebrae. In addition to fusing the vertebrae together, another surgical goal of spinal implantation may be to distract the vertebrae apart, to prevent the vertebrae from compressing the nerve roots which may cause pain or even paralysis.

In some examples, fusion surgery outcomes may be limited by the vertebral endplate area in contact with a fusion device implanted between the vertebrae. In an illustrative example, placing a spinal implant large enough to stabilize the vertebral bodies within a collapsed disc space may be difficult. In various scenarios, desirable post-surgical spinal stability or subsequent bone growth may be limited by the spinal implant's surface area in contact with the adjacent vertebral endplates.

SUMMARY

Apparatus and associated methods relate to a spinal implant configured to expand both vertically and laterally at the same time when wedges coupled by a threaded post drive movable spinal implant endplates radially outward from the longitudinal axis of the threaded post, displacing the wedges and expanding the implant as the threaded post turns. In an illustrative example, the wedges may be a pair of wedges configured with dual inclined planes. The inclined planes may be, for example, disposed both vertically and laterally with respect to the threaded post longitudinal axis, permitting implant expansion both vertically and laterally simultaneously. In some examples, the wedges may be cones. Some embodiments may include an aligning support. In some samples, the aligning support is a pair of rails adapted to prevent rotation of the wedges. Various examples may advantageously provide improved stability and reduced subsidence, based on increased vertebral body contact area with an implant expanded in place to the desired height and width.

Various embodiments may achieve one or more advantages. For example, some embodiments may reduce a surgeon's effort installing a spinal implant. This facilitation may be a result of reducing the surgeon's effort adjusting the spinal implant within a collapsed disc space during implant surgery, based on providing a spinal implant designed to expand both vertically and laterally at the same time. In an illustrative example, an embodiment spinal implant designed to expand both vertically and laterally at the same time may permit a surgeon to implant a smaller device between vertebrae, and then expand the implant in situ. Some examples may provide improved implant surgery outcomes. This facilitation may be a result of improved fusion surgery results based on a spinal implant that improves spinal stability and reduces implant subsidence into the vertebral endplates by increasing the area of contact between the spinal implant and the vertebral endplates. Some embodiments may reduce post-surgical spinal pain. Such reduced post-surgical spinal pain may be a result of providing a spinal implant that can be adjusted during surgery to a height and width effective to improve structural stability of the patient's spinal column, thereby helping the implant keep the vertebrae apart to prevent pain due to pressure on the nerve roots. In some embodiments, post-surgical structural stability of the patient's spine may be improved. Such improved spinal stability may be a result of an implant that is expandable both vertically and laterally at the same time, to increase the implant's contact surface area engaged with vertebral bodies in the patient's spine. Additionally, such improved spinal stability may be a result of an implant configured with bone graft material, such as bone graft material, to promote bone growth and fusion between the implant and vertebral bodies after installation of the implant in the patient's spine.

Various embodiments may improve spinal fusion surgical outcomes. Such improved surgical outcomes for spinal fusion surgery may be a result of reducing the structural load placed against the weakest parts of the vertebral bodies, based on providing a spinal implant that increases the surface area of contact between the implant and the vertebral bodies to reduce cavitation of the implant into the vertebrae. Some implementations may reduce the risk of damage to the vertebrae. This facilitation may be a result of maintaining the space between the vertebral bodies separated by the implant, based on improved post-surgical bone growth fusion resulting from an increased area of contact between the spinal implant and the vertebral endplates. In some examples, a spinal implant expandable both vertically and laterally at the same time may help solve the problem of placing an implant in a collapsed disc space by allowing a surgeon to implant a smaller spinal implant device between the vertebrae, and then expanding the smaller spinal implant in situ, effectively expanding the spinal implant to a size large enough to distract the vertebral posterior elements and relieve pressure on the nerve root. Various embodiments may improve post-surgical fusion surgery bone growth. This facilitation may be a result of a spinal implant expandable both vertically and laterally at the same time to increase the amount of bone graft material that may be used with the implant, based on increasing the area of graft material that is able to contact the vertebral endplates.

The details of various embodiments are set forth in the accompanying drawings and the description below. Other features and advantages will be apparent from the description and drawings, and from the claims.

BRIEF DESCRIPTION OF THE DRAWINGS

Accompanying this written specification is a collection of drawings of exemplary embodiments of the present invention. One of ordinary skill in the art would appreciate that these are merely exemplary embodiments, and additional and alternative embodiments may exist and still be within the spirit of the invention as described herein.

DETAILED DESCRIPTION OF ILLUSTRATIVE EMBODIMENTS

To aid understanding, this document is organized as follows. First, illustrative usage of an exemplary vertically and laterally expandable spinal implant configured with a pair of bi-planar wedges adapted to drive movable spinal implant endplates radially outward from the longitudinal axis of a threaded post, displacing the wedges as the threaded post turns, is briefly introduced with reference to FIG. 1. Then, with reference to FIGS. 2-10, the discussion turns to exemplary embodiments that illustrate the design and operation of exemplary vertically and laterally expandable spinal implant implementations. Specifically, various views of an exemplary vertically and laterally expandable spinal implant depicted in illustrative configurations are disclosed, to explain improvements in spinal implant design.

Figure 1:
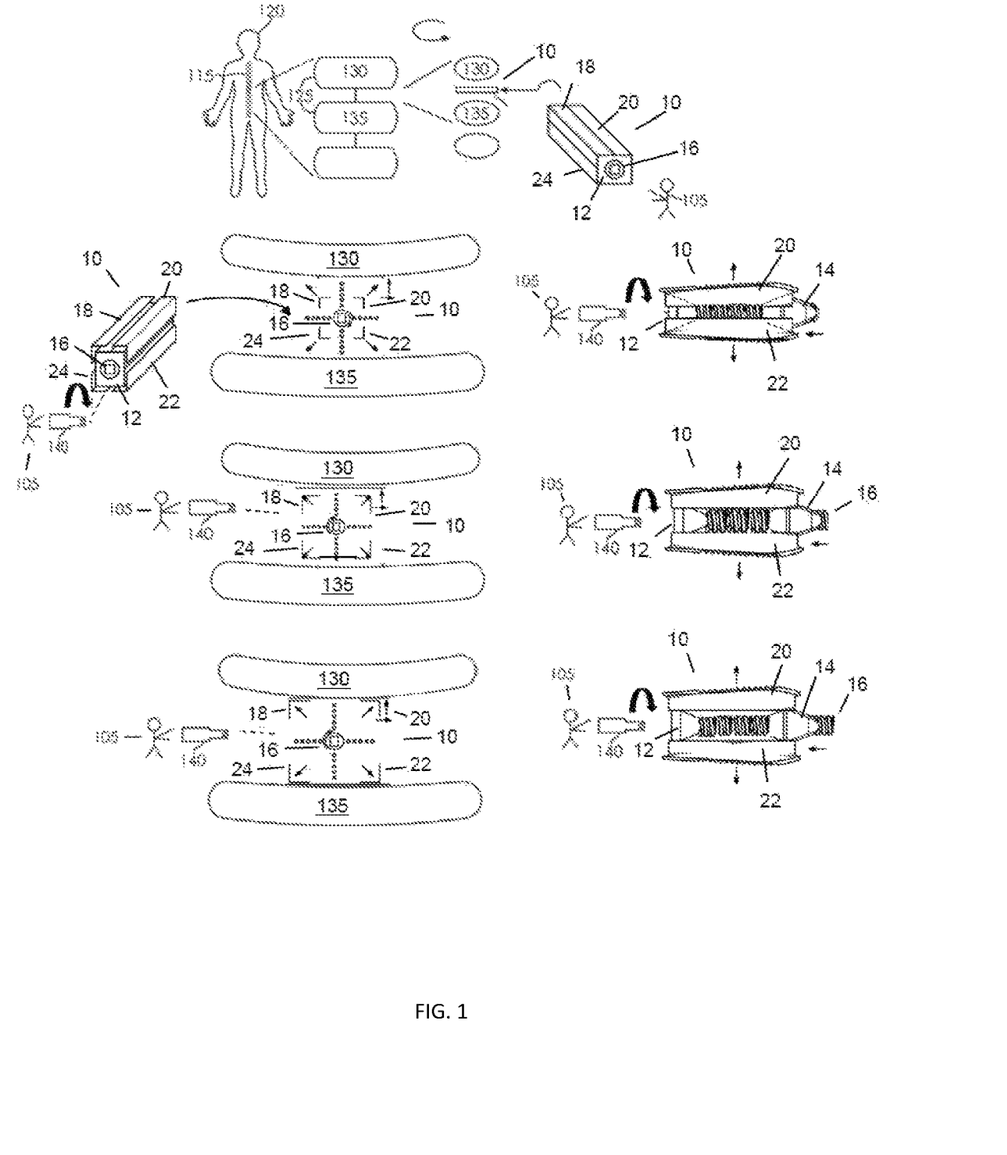
FIG. 1 depicts an illustrative operational scenario wherein a surgeon implants an exemplary spinal implant configured to expand both vertically and laterally at the same time when wedges coupled by a threaded post drive movable spinal implant endplates radially outward from the longitudinal axis of the threaded post, displacing the wedges and expanding the implant as the threaded post turns.

FIG. 1 depicts an illustrative operational scenario wherein a surgeon implants an exemplary spinal implant configured to expand both vertically and laterally at the same time when wedges coupled by a threaded post drive movable spinal implant endplates radially outward from the longitudinal axis of the threaded post, displacing the wedges and expanding the implant as the threaded post turns. In FIG. 1, the surgeon 105 inserts the spinal implant 10 within the spine 115 of the patient 120. In the depicted example, the surgeon 105 inserts the spinal implant 10 between the pair of vertebrae 125. In the illustrated example, the surgeon 105 inserts the spinal implant 10 between superior vertebral endplate 130 and inferior vertebral endplate 135 of the pair of vertebrae 125 in the patient 120 spine 115. In the illustrated example, the surgeon 105 rotationally drives spinal implant 10 threaded post 16 with spinal implant installation tool fastener. In the illustrated embodiment, the threaded post 16 axially couples the posterior wedge 12 to the anterior wedge 14. In the depicted embodiment, the threaded post 16 is configured to spin within the posterior wedge 12 and the anterior wedge 14. In the depicted example, the anterior wedge 14 moves axially along the threaded post 16 toward the posterior wedge 12, as the surgeon 105 turns the threaded post 16. In the depicted example, the spinal implant 10 includes four movable endplates 18, 20, 22, and 24, arranged between the posterior wedge 12 and the anterior wedge 14. In the illustrated embodiment, each endplate 18, 20, 22, and 24 is configured with an interior angled face 68 slidably resting on the posterior wedge 12 and the anterior wedge 14. In the depicted embodiment, the posterior wedge 12 and the anterior wedge 14 are both bi-planar wedges, configured such that each wedge includes two inclined plane wedge faces. In the illustrated embodiment, each of the posterior wedge 12 and the anterior wedge 14 include a first wedge face with an incline disposed vertically with respect to the threaded post 16 longitudinal axis. In the depicted embodiment, each of the posterior wedge 12 and the anterior wedge 14 also include a second wedge face with an incline disposed laterally with respect to the threaded post 16 longitudinal axis. In the depicted example, the anterior wedge 14 is pulled posteriorly toward the posterior wedge 12 as the surgeon 105 turns the threaded post 16. In the illustrated embodiment, the action of pulling the anterior wedge 14 toward the posterior wedge 12 forces the endplates 18, 20, 22, and 24 to ride against the wedges. In the depicted embodiment, the endplates 18, 20, 22, and 24 are forced further apart from one another by riding against the anterior wedge 14 and the posterior wedge 12. In the illustrated embodiment, as the threaded post 16 turns, the moving endplates 18, 20, 22, and 24 expand the spinal implant 10 both vertically and laterally at the same time, because the anterior wedge 14 and posterior wedge 12 are bi-planar.

In the depicted example, the threaded post 16 is able to spin within both the posterior wedge 12 and the anterior wedge 14. In the illustrated example, the threaded post 16 is rotatably captured within the posterior wedge 12 so that it can only spin, but cannot move longitudinally or laterally in reference to the posterior wedge 12. In an illustrative example, the threaded portion of the threaded post 16 may not engage the posterior wedge 12. In the illustrated embodiment, the threaded portion of the threaded post 16 engages with the threaded portion of the anterior wedge 14. In the depicted example, the threaded post 16 moves the anterior wedge 14 axially along the threaded post 16 threads as the threaded post 16 spins. In an illustrative practical example, the anterior wedge 14 moves towards the posterior wedge 12 as the threaded post 16 turns.

In the depicted example, both the anterior 14 and posterior wedges 12 have angular, or wedged, faces in two planes. In the illustrated embodiment, the superior and inferior faces of the anterior wedge 14 and the posterior wedge 12 are at an angle to one another. In addition, the lateral faces of the of the anterior wedge 14 and the posterior wedge 12 are also at an angle to one another. In the illustrated embodiment, the endplates 18, 20, 22, and 24 are arranged between the anterior wedge 14 and posterior wedge 12. In the depicted example, each endplate 18, 20, 22, and 24 has at least one interior angled face 68. In the illustrated example, the interior angled faces 68 of the endplates 18, 20, 22, and 24 rest upon the angled faces of the anterior wedge 14 and the posterior wedge 12. In an example illustrative of the similar endplate 20, 22, and 24 structures, the upper left endplate 18 has four interior angled faces 68. For example, one lateral, posterior angled face rests against the lateral face of the posterior wedge 12, while the inferior, posterior angled face of the upper left endplate 18 rests against the superior face of the posterior wedge 12. Correspondingly, the lateral, anterior angled face rests against the lateral face of the anterior wedge 14, while the inferior, anterior angled face of the upper left endplate 18 rests against the superior face of the anterior wedge 14.

In the illustrated example, as the threaded post 16 is turned, the threaded post 16 pulls the anterior wedge 14 posteriorly toward the posterior wedge 12, forcing the endplates 18, 20, 22, and 24 to ride against the wedges, which drive the endplates 18, 20, 22, and 24 further apart from one another. In the depicted example, because the anterior 14 and posterior wedges 12 are bi-planar, the movable endplates 18, 20, 22, and 24 expand the spinal implant 10 both vertically and laterally at the same time, as the threaded post 16 turns.

Figure 2:
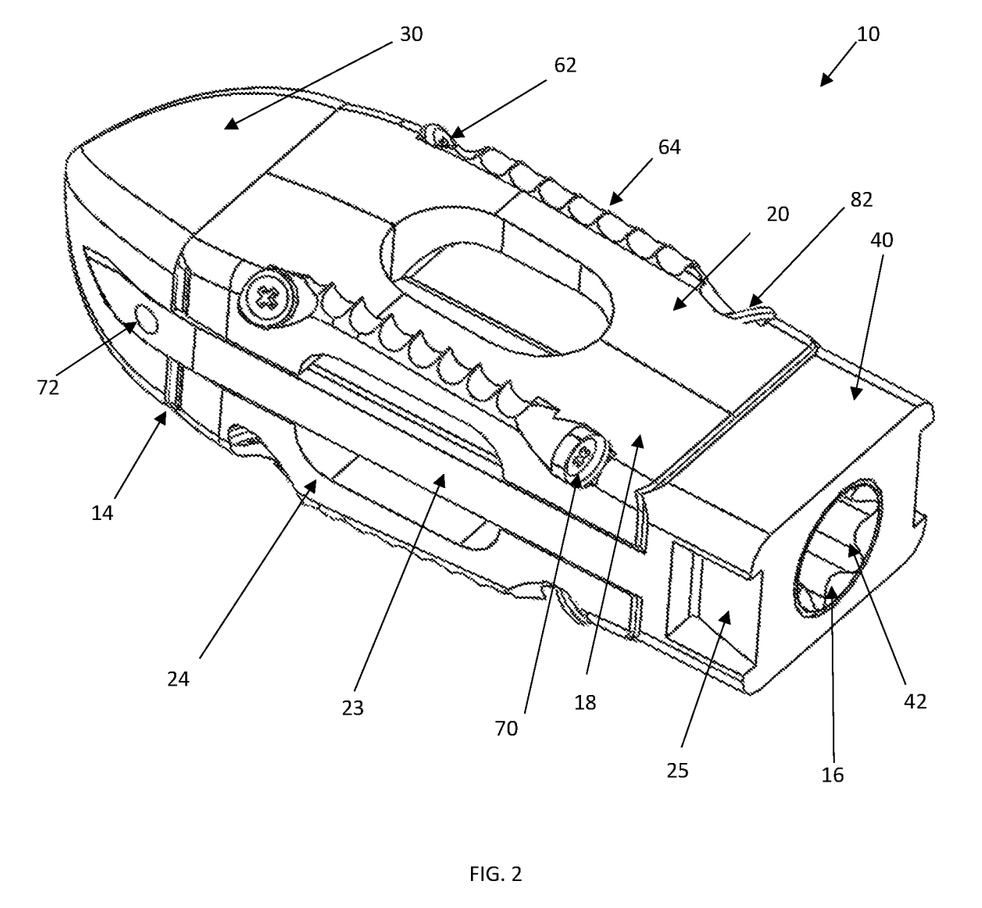
FIG. 2 depicts a top, rear perspective view of an embodiment spinal implant in an illustrative unexpanded configuration.

FIG. 2 depicts a top, rear perspective view of an embodiment spinal implant in an illustrative unexpanded configuration. In FIG. 2, the exemplary unexpanded spinal implant 10 includes a posterior base 40 axially coupled with an anterior base 30 by the threaded post 16. In the depicted example, endplates 18, 20, 22, and 24 include ridges 64 configured to bite into the vertebral endplate and secure the implant 10 to the spine. In some examples, the posterior base 40 includes an aligning support. In the illustrated embodiment, the aligning support comprises a pair of rails 23 which laterally extend towards the anterior wedge 14 and the anterior base 30 and are configured to engage with anterior wedge rail inserts 56 and the anterior base rail inserts 32. In the depicted embodiment, connectors 72 connect the rails 23 to the anterior base 30. In some embodiments, the connectors 72 may include pins, screws, clips, clasps or other connecting members. In the depicted embodiment, the posterior base 40 includes indentations 25 on the lateral edge to allow for an inserter (not shown) to hold the implant 10. In the illustrated embodiment, an opening 28 in the posterior base 40 accepts the threaded post 16, permitting rotation of the threaded post 16 within the posterior base 40. In the depicted example, the opening 28 also has a beveled interior edge to prevent the threaded post 16 from displacing anteriorly.

Figure 3:
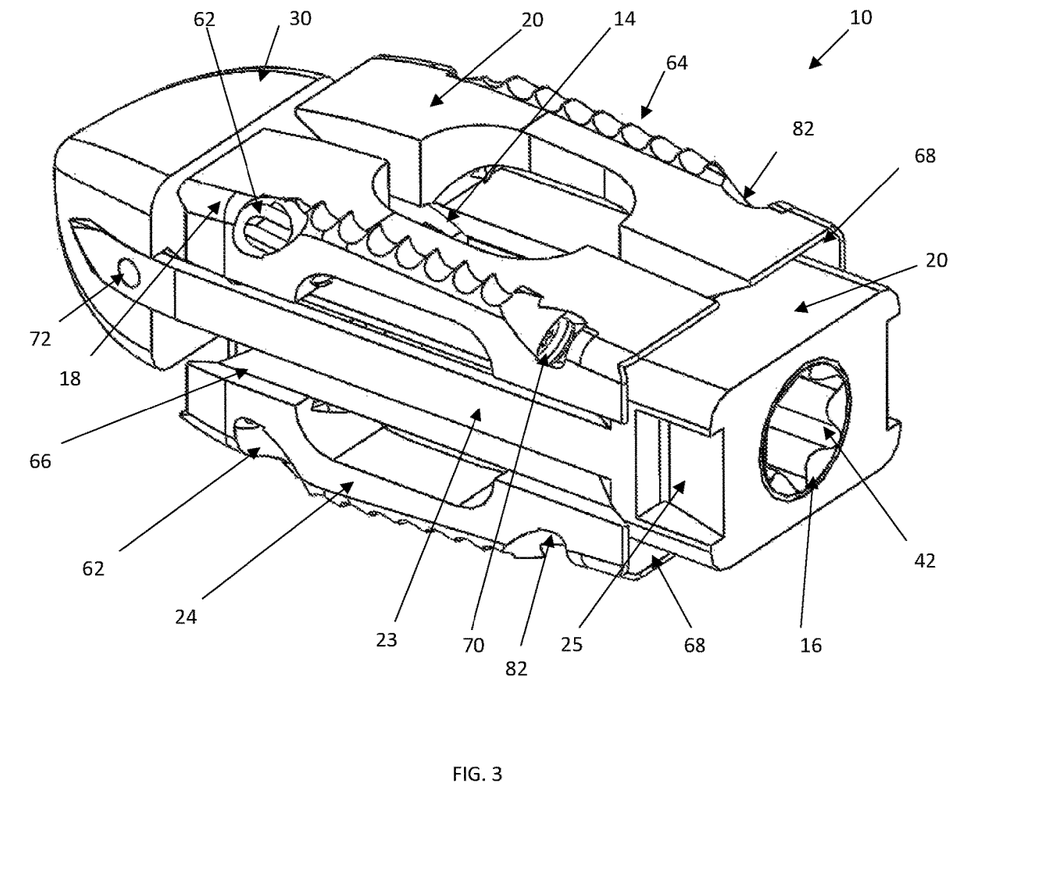
FIG. 3 depicts a top, rear perspective view of an embodiment spinal implant in an illustrative expanded configuration.

FIG. 3 depicts a top, rear perspective view of an embodiment spinal implant in an illustrative expanded configuration. In FIG. 3, the embodiment spinal implant 10 is depicted in an exemplary partially expanded configuration illustrating the endplates 18, 20, 22, and 24 radially displaced from the threaded post 16 longitudinal axis. In the depicted embodiment, the posterior wedge 12 extends from the posterior base 40. In the illustrated embodiment, the endplates 18, 20, 22, and 24 are radially displaced from the threaded post 16 longitudinal axis as a result of the anterior wedge 14 moving away from the anterior base 30 and toward the posterior wedge 12, as the threaded post 16 was turned, to expand the spinal implant 10 both vertically and laterally at the same time. In some embodiments, a linking element connects the anterior end of the endplates 18, 20, 22, and 24 to the anterior wedge 14. In some embodiments, a linking element connects the posterior end of the endplates 18, 20, 22, and 24 to the posterior wedge 12. In some examples, the linking element prevents the implant from over-expanding. In the illustrated example, the linking element includes holes 54 disposed on the anterior and posterior wedges 14 and 12, aligned with openings 62 disposed on the endplates 18, 20, 22, and 24 configured to retain fasteners 70. In some embodiments, the fasteners 70 may be screws, pins, glue and other fasteners. In some examples, the fasteners 70 are inserted through the openings 62 and into holes 54 to connect the endplates 18, 20, 22, and 24 to each of the anterior wedge 14 and the posterior wedge 12. In some embodiments, as the endplates 18, 20, 22, and 24 are radially displaced from the threaded post 16, the fasteners 70 limit the vertical and lateral expansion of the endplates 18, 20, 22, and 24. For example, the fasteners 70 may limit the vertical and lateral expansion of the endplates 18, 20, 22, and 24 by pivoting, sliding, or otherwise moving while staying engaged with both the endplates 18, 20, 22, and 24 and the anterior and posterior wedges 12 and 14. In the depicted embodiment, the anterior portion of the endplates 18, 20, 22, and 24 maintains engagement with the anterior wedge 12 and the posterior portion of the endplates 18, 20, 22, and 24 maintains engagement with the posterior wedge 14.

Figure 4:
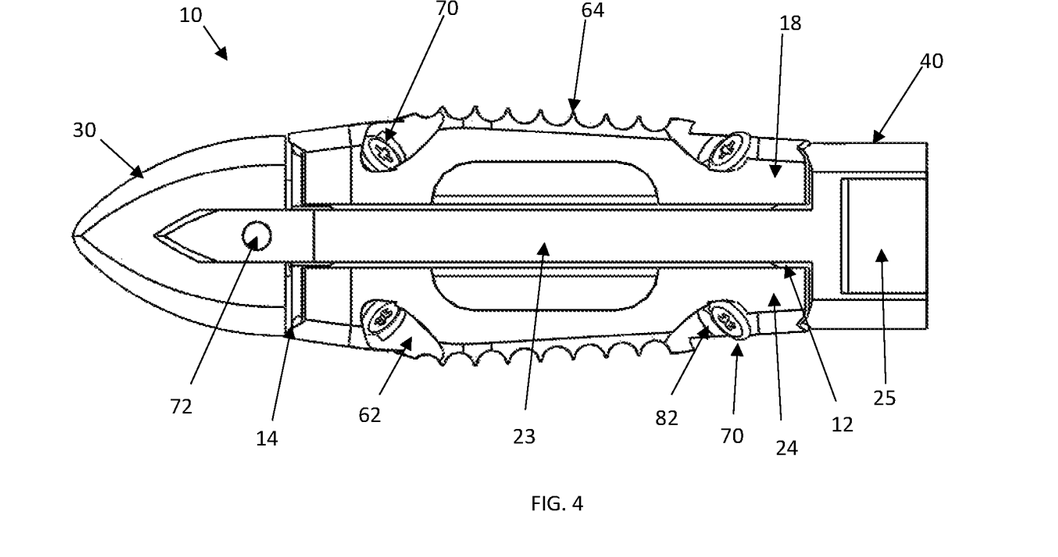
FIG. 4 depicts a side view of an embodiment spinal implant in an illustrative unexpanded configuration.

FIG. 4 depicts a side view of an embodiment spinal implant in an illustrative unexpanded configuration. In FIG. 4, the depicted side view of the exemplary unexpanded spinal implant 10 includes the posterior base 30 axially coupled with the anterior wedge 14 by a threaded post. As shown in the illustrated example, in the unexpanded position, the anterior wedge 14 rests against the anterior base 30. In the depicted example, the left lateral rail 23 and the right lateral rail (not shown) extend from the posterior base 40. In the illustrated example, the rails 23 are connected to the anterior base 30 by connectors 72. In the depicted example, the threaded post is obscured from view by the rail 23, upper right endplate 20, the lower right endplate 22, the anterior base 40, the anterior wedge 14, the posterior base 30 and the posterior wedge 12. The endplates 18, 20, 22, and 24 include ridges 64 and fasteners 70 to limit the movement of the anterior wedge 14 and the radial expansion of the endplates 18, 20, 22, and 24. For example, the fasteners 70 may limit the vertical and lateral expansion of the endplates 18, 20, 22, and 24 by pivoting, sliding, or otherwise moving while staying engaged with both the endplates 18, 20, 22, and 24 and the anterior and posterior wedges 12 and 14. In the depicted embodiment, the anterior portion of the endplates 18, 20, 22, and 24 maintains engagement with the anterior wedge 12 and the posterior portion of the endplates 18, 20, 22, and 24 maintains engagement with the posterior wedge 14.

Figure 5:
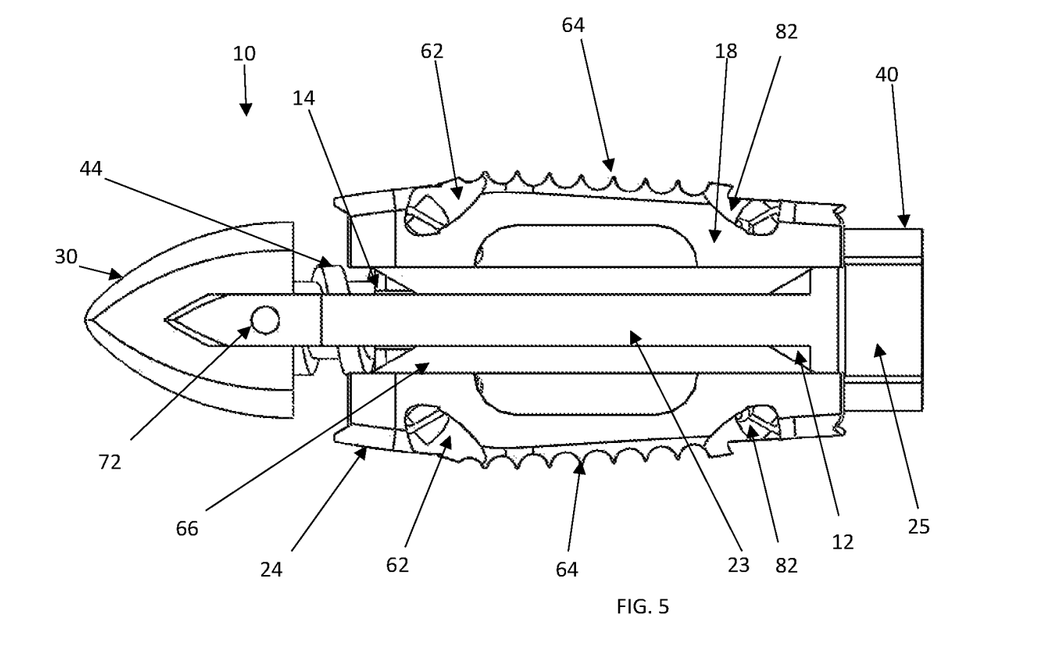
FIG. 5 depicts side view of an embodiment spinal implant in an illustrative expanded configuration.

FIG. 5 depicts a side view of an embodiment spinal implant in an illustrative expanded configuration. In FIG. 5, the depicted side view of the exemplary partially expanded spinal implant 10 includes the posterior wedge 12 and the posterior base 40 axially coupled with the anterior wedge 14 by the threaded post 16. In the illustrated embodiment, the upper left endplate 18 rests against the posterior wedge 12 superior face and the posterior wedge 12 left lateral face. In the depicted embodiment, the upper left endplate 18 also rests against the anterior wedge 14 superior face and the anterior wedge 14 left lateral face. In the illustrated embodiment, the exemplary spinal implant 10 includes a lower left endplate resting against the posterior wedge 12 inferior face and the posterior wedge 12 left lateral face. In the depicted embodiment, the lower left endplate also rests against the anterior wedge 14 inferior face and the anterior wedge 14 left lateral face. In the depicted embodiment, the upper right endplate 20 is obscured from view. In the illustrated embodiment, the upper right endplate 20 rests against the posterior wedge 12 superior face and the posterior wedge 12 right lateral face. In the depicted embodiment, the upper right endplate 20 also rests against the anterior wedge 14 superior face and the anterior wedge 14 right lateral face. In the depicted example, the lower right endplate is obscured from view. In the illustrated embodiment, the lower right endplate 22 rests against the posterior wedge 12 inferior face and the posterior wedge 12 right lateral face. In the depicted embodiment, the lower right endplate 22 also rests against the anterior wedge 14 inferior face and the anterior wedge 14 right lateral face. In the illustrated example, the threaded post 16 is visible behind the rail 23. In the depicted example, the upper left endplate 18 and the lower left endplate 24 are radially displaced from the threaded post 16 longitudinal axis as a result of the anterior wedge 14 moving toward the posterior wedge 12, as the threaded post 16 was turned. The fasteners 70 in the endplates 18, 20, 22, and 24 limit the movement of the anterior wedge 14 and the radial expansion of the endplates 18, 20, 22, and 24. For example, the fasteners 70 may limit the vertical and lateral expansion of the endplates 18, 20, 22, and 24 by pivoting, sliding, or otherwise moving while staying engaged with both the endplates 18, 20, 22, and 24 and the anterior and posterior wedges 12 and 14. In the depicted embodiment, the anterior portion of the endplates 18, 20, 22, and 24 maintains engagement with the anterior wedge 12 and the posterior portion of the endplates 18, 20, 22, and 24 maintains engagement with the posterior wedge 14.

Figure 6:
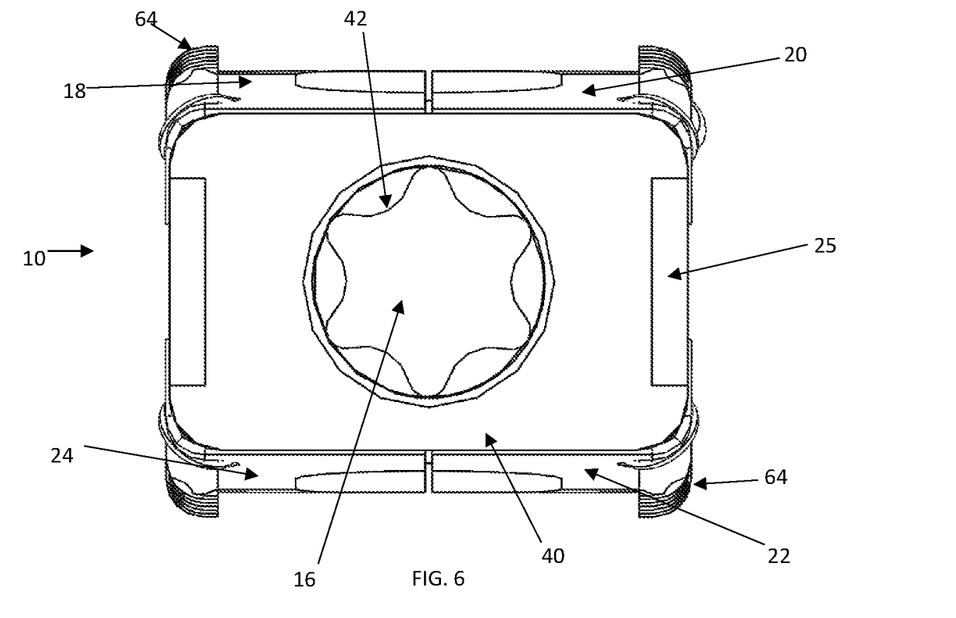
FIG. 6 depicts a rear view of an embodiment spinal implant in an illustrative unexpanded configuration.

FIG. 6 depicts a rear view of an embodiment spinal implant in an illustrative unexpanded configuration. In FIG. 6, the depicted rear view of the exemplary unexpanded spinal implant 10 includes the posterior base 40 engaged with the threaded post 16 having a driver profile 42. In some examples, an inserter (not shown) may engage with the driver profile 42 to rotate the threaded post 16. In the illustrated example, the posterior base 40 includes indentations 25 on each lateral edge to allow for an inserter (not shown) to hold the implant 10. In the depicted example, the end plates 18, 20, 22, and 24 are visible above and below the posterior wedge 12. In the illustrated embodiment, the end plates 18, 20, 22, and 24 include ridges 64 configured to bite into the vertebral endplate and secure the implant 10 to the spine.

Figure 7:
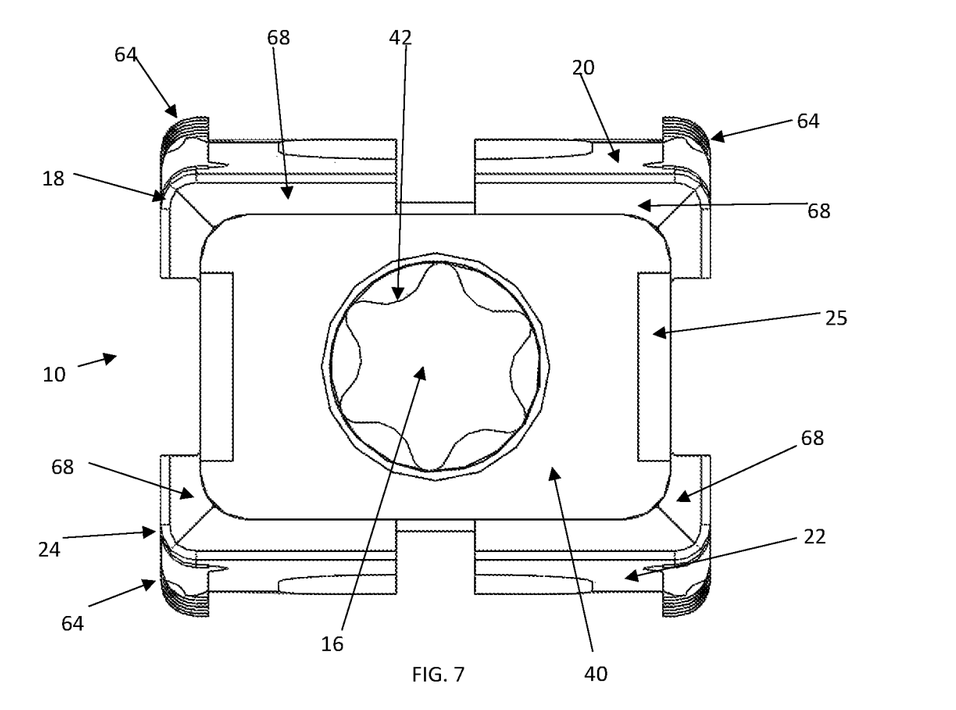
FIG. 7 depicts a rear view of an embodiment spinal implant in an illustrative expanded configuration.

FIG. 7 depicts a rear view of an embodiment spinal implant in an illustrative expanded configuration. In FIG. 7, the depicted rear view of the exemplary partially expanded spinal implant the depicted rear view of the exemplary unexpanded spinal implant 10 includes the posterior base 40 engaged with the threaded post 16 having a driver profile 42. In the illustrated example, the posterior wedge 12 includes indentations 25 on each lateral edge to allow for an inserter (not shown) to hold the implant 10. In the depicted example, the upper right endplate 20 and the upper left endplate 18 are radially displaced from the threaded post 16 longitudinal axis as a result of the anterior wedge 14 moving toward the posterior wedge 12, as the threaded post 16 was turned. In the illustrated example, the lower right endplate 22 and the lower left endplate 24 are radially displaced from the threaded post 16 longitudinal axis as a result of the anterior wedge 14 moving toward the posterior wedge 12, as the threaded post 16 was turned.

Figure 8:
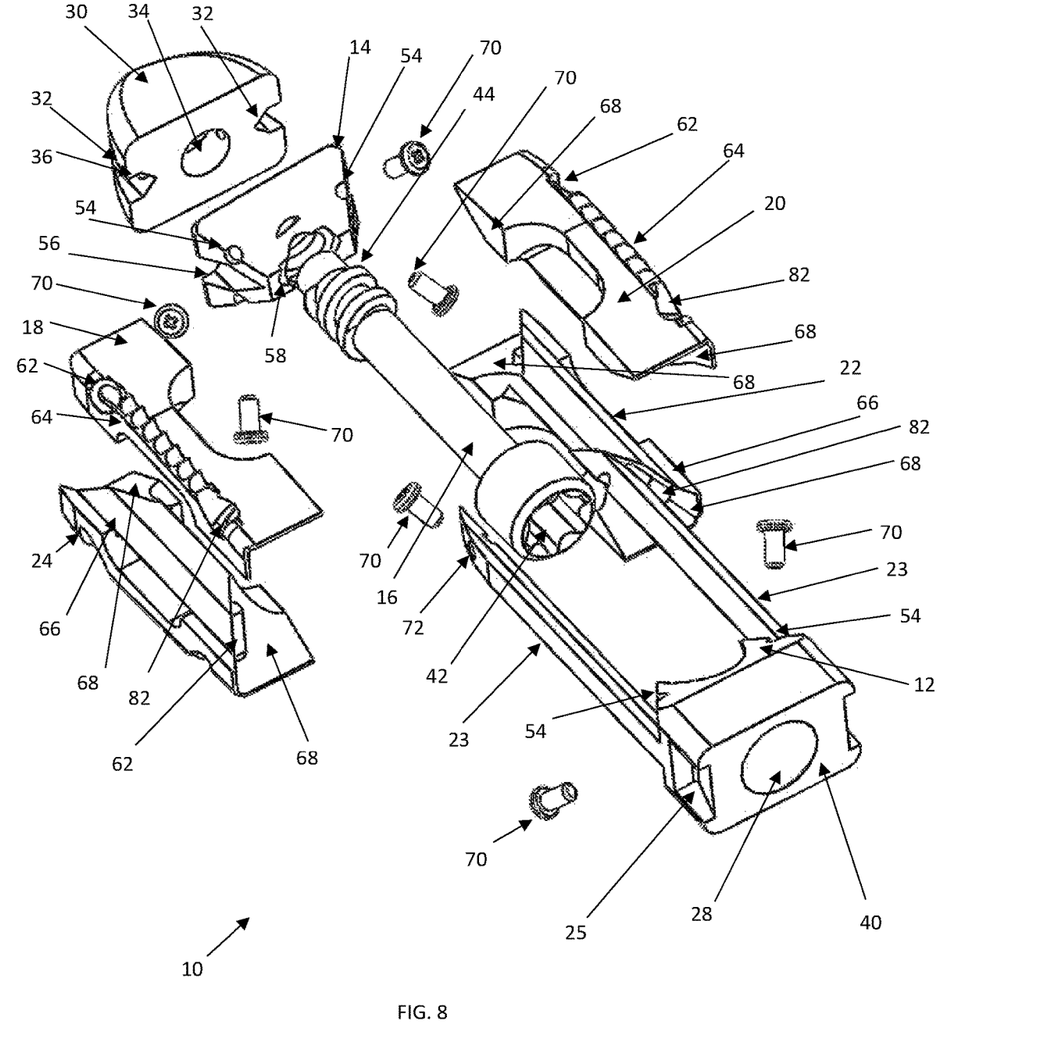
FIG. 8 depicts a top, rear perspective view of an embodiment spinal implant in an illustrative exploded configuration.

FIG. 8 depicts a top, rear perspective view of an embodiment spinal implant in an illustrative exploded configuration. In FIG. 8, the depicted top, rear perspective view of the exemplary spinal implant 10 in the illustrated exploded configuration includes the threaded post 16, the posterior base 40, the posterior wedge 12, the anterior base 30, the anterior wedge 14, the upper left endplate 18, the lower left endplate 24, the upper right endplate 20, and the lower right endplate 22. In the illustrated example, the threaded shaft 16 includes a threaded portion 44 and a driver profile 42. In the depicted embodiment, the anterior base 30 includes an anterior base post receiver 34 for receiving the threaded post 16. In some embodiments, the anterior base post receiver 34 is configured to permit rotation of the threaded post 16 within the posterior base 40. In the illustrated example, the anterior wedge 14 includes an anterior wedge post receiver 58 configured to permit rotation of the threaded post 16 within the anterior wedge 14. In some embodiments, at least a portion of the interior of the anterior wedge post receiver 58 is threaded, corresponding to the threaded portion of the threaded post 16. In an illustrative example, as the threaded post 16 is turned, the anterior wedge 14 moves toward the posterior wedge 12.

Figure 9:
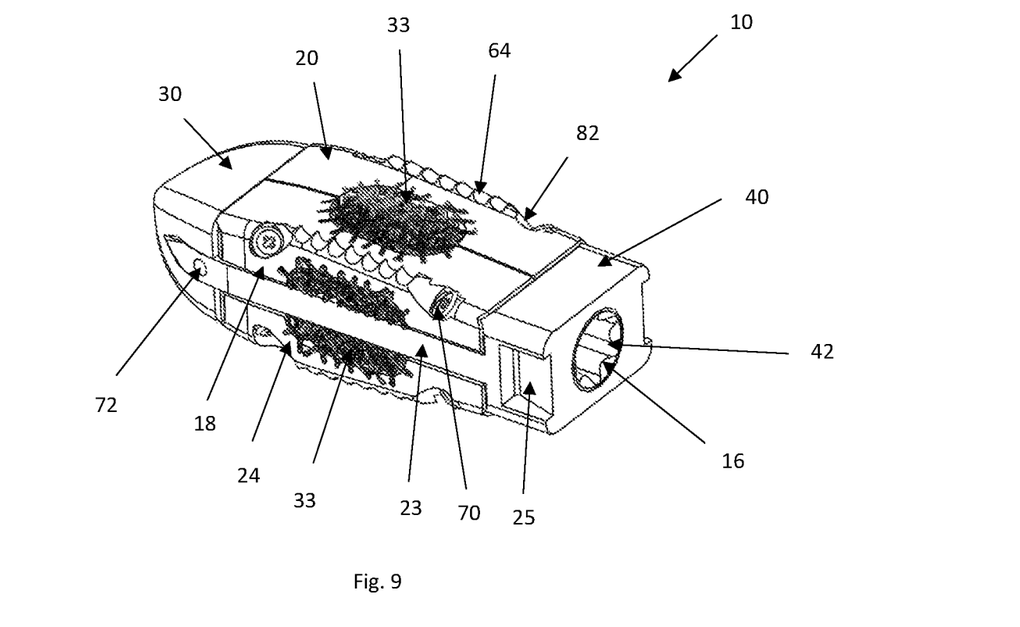
FIG. 9 depicts a top, rear perspective view of an embodiment spinal implant configured with bone graft material in an illustrative unexpanded configuration.

FIG. 9 depicts a top, rear perspective view of an embodiment spinal implant configured with bone graft material in an illustrative unexpanded configuration. In FIG. 9, the exemplary unexpanded spinal implant 10 includes a posterior base 40 axially coupled with an anterior base 30 by the threaded post 16. In the depicted example, endplates 18, 20, 22, and 24 include ridges 64 configured to bite into the vertebral endplate and secure the implant 10 to the spine. In the illustrated example, each of the endplates 18, 20, 22, and 24 includes at least one recess configured to receive the bone graft material 33. In the depicted example, the endplates 18, 20, 22, and 24 and the bone graft material 33 are configured to maintain contact with the vertebral body once the spinal implant 10 is implanted. In the illustrated embodiment, at least a portion of the bone graft material 33 is porous.

Figure 10:
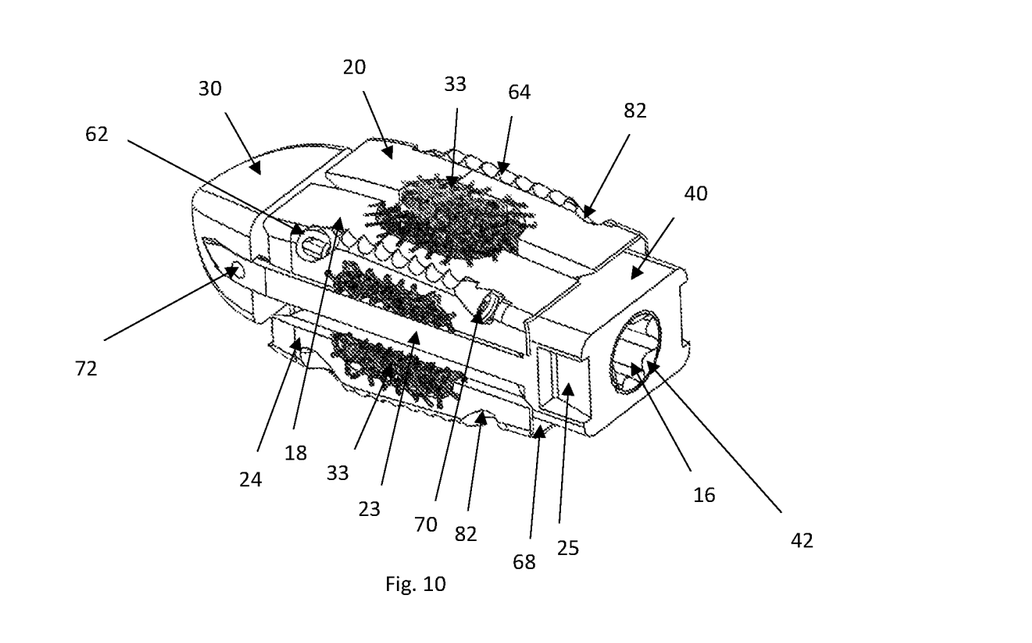
FIG. 10 depicts a top, rear perspective view of an embodiment spinal implant configured with bone graft material in an illustrative expanded configuration.

FIG. 10 depicts a top, rear perspective view of an embodiment spinal implant configured with bone graft material in an illustrative expanded configuration. In FIG. 10, the embodiment spinal implant 10 is depicted in an exemplary partially expanded configuration illustrating the endplates 18, 20, 22, and 24 radially displaced from the threaded post 16 longitudinal axis. In the illustrated example, each of the endplates 18, 20, 22, and 24 includes at least one recess configured to receive the bone graft material 33. In the depicted example, the endplates 18, 20, 22, and 24 and the bone graft material 33 are configured to maintain contact with the vertebral body once the spinal implant 10 is implanted. In the illustrated embodiment, at least a portion of the bone graft material 33 is porous. In the depicted embodiment, the bone graft material 33 is configured to connect with vertebral bodies when the implant 10 is in the expanded configuration.

In the illustrated embodiment, the depicted posterior wedge 12 superior face is visible. In the depicted embodiment, the illustrated anterior wedge 14 superior face, left lateral face, and right lateral faces are visible. In some embodiments, the anterior wedge 14 may have only one left lateral face. In various embodiments, the anterior wedge 14 may have only one right lateral face. In some embodiments, a linking element connects the anterior end of the endplates 18, 20, 22, and 24 to the anterior wedge 14 and the posterior end of the endplates 18, 20, 22, and 24 to the posterior wedge 12. In an illustrative example, the linking element includes holes 54 disposed on the anterior and posterior wedges 14 and 12, respectively, openings 62 on the endplates 18, 20, 22, and 24, and fasteners 70. In the depicted example, the holes 54 for accepting fasteners 70 are disposed about the intersections between two faces of the anterior wedge 14 and the intersections between two faces of the posterior wedge 12. In some example, holes 54 are disposed along the intersections. In the illustrated embodiment, the fasteners 70 connect the top endplates 18 and 20 to the interconnections between the superior faces and the lateral faces of the anterior wedge 14 and the posterior wedge 12. In the depicted example, the fasteners 70 connect the bottom endplates 22 and 24 to the interconnections between the inferior faces and the lateral faces of the anterior wedge 14 and the poster wedge 12. In some embodiments, the endplates 18, 20, 22 and 24 each include anterior and posterior openings 62, through which the fasteners 70 may be inserted. For example, endplate 18 includes an anterior opening 62 and a posterior opening 82. In an illustrative example, at least one fastener may be inserted through anterior opening 62 and into the anterior wedge 14 and at least one fastener may be inserted through posterior opening 82 and into the posterior wedge 12. For example, the fasteners 70 may limit the vertical and lateral expansion of the endplates 18, 20, 22, and 24 by pivoting, sliding, or otherwise moving while staying engaged with both the endplates 18, 20, 22, and 24 and the anterior and posterior wedges 12 and 14. In the depicted embodiment, the anterior portion of the endplates 18, 20, 22, and 24 maintains engagement with the anterior wedge 12 and the posterior portion of the endplates 18, 20, 22, and 24 maintains engagement with the posterior wedge 14.

In the depicted example, the posterior base 20 includes an aligning support. In some examples, the aligning support is a pair of rails 23 which laterally extend toward the anterior base 30 and are configured to engage with the anterior wedge rail inserts 56 to prevent the anterior wedge 14 from rotating with the threaded post 16 while the threaded post 16 is rotated and to channel the direction of the anterior wedge 14 towards the posterior wedge 12. In some embodiments, the rails 23 slidably engage with the anterior wedge rail inserts 56. In the illustrated example, the rails 23 are configured to engage with the anterior base rail inserts 32. In the depicted embodiment, the connectors 72 connect the rails 23 to the anterior base 30. In the illustrated example, each of the endplates 18, 20, 22, and 24 includes an exterior rail relief 66 configured to prevent interference between the endplates 18, 20, 22, and 24 with the rails 23. In the depicted embodiment, the posterior base 40 includes indentations 25 on the lateral edge to allow for an inserter (not shown) to hold the implant 10. In the illustrated embodiment, an opening 28 in the posterior wedge 12 and the posterior base 40 accepts the threaded post 16, permitting rotation of the threaded post 16 within the posterior wedge 12 and the posterior base 40. In some embodiments, the opening 28 also has a beveled interior edge to prevent the threaded post 16 from displacing posteriorly.

Various embodiments may improve post-surgical fusion surgery bone growth by increasing the amount of bone graft material that may be used with the implant. Some embodiments may improve post-surgical fusion surgery bone growth by increasing the area of bone graft material on or in the vertebral endplates. In the illustrated example, the endplates 18, 20, 22, and 24 are configured to receive the bone graft material 33. In the depicted example, at least a portion of the exterior surface of the endplates 18, 20, 22, and 24 includes a recess for receiving bone graft material 33. In some embodiments, the bone graft material 33 is configured to promote bone growth and fusion between the implant with vertebral bodies. In some examples, the bone graft material 33 is osteo-inductive and starts the bone fusion process, to fuse the implant to adjacent vertebral bodies.

Although various embodiments have been described with reference to the Figures, other embodiments are possible. For example, various embodiment vertical and lateral expandable spinal implant designs may include a posterior wedge and anterior wedge that are adapted to receive a threaded post axially between the two. Some embodiment implant implementations may also have four separate longitudinal moveable endplates. In an illustrative example, an implant implementation having four longitudinal moveable endplates may be configured with all four endplates aligned parallel to the threaded post. In some embodiments, each endplate may also have corresponding angled faces which mate to the wedges. In some embodiment implementations, the wedges may include wedges in two planes, both vertically and laterally. In an exemplary usage scenario, as the threaded post turns, the threaded post draws the anterior and posterior wedges toward each other axially guided by the rails extending from the posterior base. In some examples, the rails extending from the posterior base engage with the anterior wedge rail inserts and the anterior base rail inserts to prevent rotation of either or both of the anterior and posterior wedges. In some examples, the anterior wedge has an opening with an interior thread, corresponding to the threaded portion of the threaded post. In an illustrative example, the turning threaded post drawing the wedges toward each other forces the wedges against the endplates. In some scenarios, the wedges are forced outward, both vertically and horizontally, as the wedges are forced against the endplates by the turning threaded post drawing the wedges toward each other. In some examples, the posterior wedge includes indentations which enable an inserter to act as counter-torque on the implant while the threaded post is turned.

Various embodiments of the present invention generally relate to spinal implants, and more specifically, but not exclusively, concern a vertically and laterally expandable vertebral implant.

In some scenarios, persistent, often disabling, back pain can arise by disruption of the disc annulus, chronic inflammation of the disc, or relative instability of the vertebral bodies surrounding a given disc, such as might occur due to a degenerative disease. In an example illustrative of some severe cases, some form of mechanical limitation to the movement of the vertebrae on either side of the subject disc may be necessary. In such cases, the disc tissue may be irreparably damaged, thereby necessitating removal of the entire disc. However, when the disc nucleus is removed without subsequent stabilization, the same disabling back pain may reoccur due to persistent inflammation and/or instability.

Various prior art approaches illustrative of previous attempts to stabilize the adjacent vertebral bodies following excision of the disc material have been developed. However, some prior art spinal implant designs have drawbacks that lower the spinal fusion rates. Among these prior art spinal implant design drawbacks, one such design flaw is the use of interlocking dovetails to lock the implant in the expanded position. The interlocking dovetails incorporated into prior-developed spinal implants, regardless of their shape, fail to adequately lock the implant or prevent the device from over-expanding or disassembling. While a configuration incorporating interlocking dovetails may allow for easy assembly, a spinal implant requiring interlocking dovetails to lock the device in the expanded position relies on external pressure to keep the implant together and lacks an adequate mechanism to lock the implant in the proper expanded position.

In various embodiments of the present invention, an embodiment vertical and lateral expandable spinal implant includes a posterior wedge and anterior wedge that are adapted to receive a threaded post axially between the posterior wedge and anterior wedge. In some embodiments, the spinal implant also has four separate longitudinal moveable endplates. In an illustrative example, all four spinal implant endplates are aligned parallel to the threaded post. In various embodiment designs, each of the four spinal implant endplates also has corresponding angled faces which mate to the wedges. In various embodiments, the wedges are wedged in two planes, both vertically and laterally. In an illustrative example, as the threaded post turns, the threaded post draws the wedges toward each other axially guided by the rails extending from the posterior base. The rails extending from the posterior base engage with the anterior wedge rail inserts and the anterior base rail inserts to prevent rotation of either or both of the anterior and posterior wedges. In some examples, the anterior wedge has an anterior wedge post receiver with an interior thread, corresponding to the threaded portion of the threaded post. In an illustrative example, the anterior wedge post receiver configured to permit rotation of the threaded post such that as the threaded post is turned, the anterior wedge moves toward the posterior wedge. The threaded post drawing the wedges toward each other forces the wedges against the spinal implant endplates, forcing them outward, both vertically and horizontally, allowing the spinal implant to be inserted in an unexpanded, smaller configuration. As the spinal implant expands, it does so with the implant endplates moving parallel to one another, both vertically and laterally. The expansion of the endplates is limited by the linking element connecting the end plates anteriorly to the anterior wedge and posteriorly to the posterior wedge. Thereby, the movement of the various components is limited during expansion which prevents the inadvertent disassembly of the implant. In some examples, the linking element is comprised of holes disposed on the anterior and posterior wedges, aligned with the anterior and posterior wedge holes configured to retain fasteners. In some examples, the fasteners are inserted through the endplate openings and into wedge holes to connect the endplates to each of the anterior wedge and the posterior wedge. In some embodiments, as the endplates are radially displaced from the threaded post, the fasteners limit the vertical and lateral expansion of the endplates. For example, the fasteners may limit the vertical and lateral expansion of the endplates by pivoting, sliding, or otherwise moving while staying engaged with both the endplates and the anterior and posterior wedges. In some examples, the anterior portion of the endplates maintains engagement with the anterior wedge and the posterior portion of the endplates maintains engagement with the posterior wedge. Moreover, the spinal implant can distract the two vertebrae, relieving the pressure on the nerve root. Furthermore, the endplates expand laterally. This creates a wider base for the spinal implant, improving the spinal implant stability. Additionally, by expanding wider laterally, the spinal implant endplates can seat closer to the stronger apophyseal ring of the vertebrae, reducing the risk of subsidence.

In the Summary above and in this Detailed Description, and the Claims below, and in the accompanying drawings, reference is made to particular features of various embodiments of the invention. It is to be understood that the disclosure of embodiments of the invention in this specification includes all possible combinations of such particular features. For example, where a particular feature is disclosed in the context of a particular aspect or embodiment of the invention, or a particular claim, that feature can also be used—to the extent possible—in combination with and/or in the context of other particular aspects and embodiments of the invention, and in the invention generally.

While multiple embodiments are disclosed, still other embodiments of the present invention will become apparent to those skilled in the art from this detailed description. The invention is capable of myriad modifications in various obvious aspects, all without departing from the spirit and scope of the present invention. Accordingly, the drawings and descriptions are to be regarded as illustrative in nature and not restrictive.

It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments.

In the present disclosure, various features may be described as being optional, for example, through the use of the verb "may;", or, through the use of any of the phrases: "in some embodiments," "in some implementations," "in some designs," "in various embodiments," "in various implementations,", "in various designs," "in an illustrative example," or "for example;" or, through the use of parentheses. For the sake of brevity and legibility, the present disclosure does not explicitly recite each and every permutation that may be obtained by choosing from the set of optional features. However, the present disclosure is to be interpreted as explicitly disclosing all such permutations. For example, a system described as having three optional features may be embodied in seven different ways, namely with just one of the three possible features, with any two of the three possible features or with all three of the three possible features.

In various embodiments. elements described herein as coupled or connected may have an effectual relationship realizable by a direct connection or indirectly with one or more other intervening elements.

In the present disclosure, the term "any" may be understood as designating any number of the respective elements, i.e. as designating one, at least one, at least two, each or all of the respective elements. Similarly, the term "any" may be understood as designating any collection(s) of the respective elements, i.e. as designating one or more collections of the respective elements, a collection comprising one, at least one, at least two, each or all of the respective elements. The respective collections need not comprise the same number of elements.

While various embodiments of the present invention have been disclosed and described in detail herein, it will be apparent to those skilled in the art that various changes may be made to the configuration, operation and form of the invention without departing from the spirit and scope thereof. In particular, it is noted that the respective features of embodiments of the invention, even those disclosed solely in combination with other features of embodiments of the invention, may be combined in any configuration excepting those readily apparent to the person skilled in the art as nonsensical. Likewise, use of the singular and plural is solely for the sake of illustration and is not to be interpreted as limiting.

In the present disclosure, all embodiments where "comprising" is used may have as alternatives "consisting essentially of," or "consisting of." In the present disclosure, any method or apparatus embodiment may be devoid of one or more process steps or components. In the present disclosure, embodiments employing negative limitations are expressly disclosed and considered a part of this disclosure.

Certain terminology and derivations thereof may be used in the present disclosure for convenience in reference only and will not be limiting. For example, words such as "upward," "downward," "left," and "right" would refer to directions in the drawings to which reference is made unless otherwise stated. Similarly, words such as "inward" and "outward" would refer to directions toward and away from, respectively, the geometric center of a device or area and designated parts thereof. References in the singular tense include the plural, and vice versa, unless otherwise noted.

The term "comprises" and grammatical equivalents thereof are used herein to mean that other components, ingredients, steps, among others, are optionally present. For example, an embodiment "comprising" (or "which comprises") components A, B and C can consist of (i.e., contain only) components A, B and C, or can contain not only components A, B, and C but also contain one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example, "at least 1" means 1 or more than 1. The term "at most" followed by a number (which may be a range having 1 or 0 as its lower limit, or a range having no lower limit, depending upon the variable being defined). For example, "at most 4" means 4 or less than 4, and "at most fastener %" means fastener % or less than fastener %. When, in this specification, a range is given as "(a first number) to (a second number)" or "(a first number)-(a second number)," this means a range whose limit is the second number. For example, 25 to 100 mm means a range whose lower limit is 25 mm and upper limit is 100 mm.

Many suitable methods and corresponding materials to make each of the individual parts of embodiment apparatus are known in the art. According to an embodiment of the present invention, one or more of the parts may be formed by machining, 3D printing (also known as "additive" manufacturing), CNC machined parts (also known as "subtractive" manufacturing), and injection molding, as will be apparent to a person of ordinary skill in the art. Metals, wood, thermoplastic and thermosetting polymers, resins and elastomers as may be described herein-above may be used. Many suitable materials are known and available and can be selected and mixed depending on desired strength and flexibility, preferred manufacturing method and particular use, as will be apparent to a person of ordinary skill in the art.

Any element in a claim herein that does not explicitly state "means for" performing a specified function, or "step for" performing a specific function, is not to be interpreted as a "means" or "step" clause as specified in 35 U.S.C. § 112 (f). Specifically, any use of "step of" in the claims herein is not intended to invoke the provisions of 35 U.S.C. § 112 (f).

A number of implementations have been described. Nevertheless, it will be understood that various modifications may be made. For example, advantageous results may be achieved if the steps of the disclosed techniques were performed in a different sequence, or if components of the disclosed systems were combined in a different manner, or if the components were supplemented with other components. Accordingly, other implementations are contemplated within the scope of the following claims.

What is claimed is:

1. An apparatus, comprising:
   a spinal implant configured to expand in at least two dimensions at the same time, comprising:
   a first base connected to a first wedge and a pair of support rails extending from a first side of the first base;
   a second base statically coupled to the first base by the pair of rails;
   a second wedge separate from the second base and movably disposed between the first base and the second base, the second wedge coupled with the first base by a threaded post rotatably retained by the first base and a threaded aperture configured in the second wedge; and,
   a plurality of endplates each of the plurality of endplates having one or more linking elements connecting each endplate to each of the first wedge and the second wedge, and wherein each endplate of the plurality of endplates is slidably engaged with the first wedge and the second wedge.

2. The apparatus of claim 1, wherein the first wedge and the pair of support rails are integrally formed with and extending from a first side of the first base.

3. The apparatus of claim 1, wherein each support rail of the pair of support rails has one or more angled medial faces that are smooth.

4. The apparatus of claim 1, wherein the second base is formed with a rail insert on two opposing sides of the second base and each of the rail inserts is configured to receive one of the supporting rails.

5. The apparatus of claim 1, wherein the second wedge slides along the pair supporting rails between the first base and the second base.

6. The apparatus of claim 1, wherein the linking element limits the lateral and vertical expansion of the endplates.

7. The apparatus of claim 6, wherein the linking element is comprised of fasteners adapted to engage each of the plurality of end plates with each of the first wedge and the second wedge.

8. The apparatus of claim 1, wherein the first wedge or the second wedge further comprise a dove tail member running along the corners of the wedge's angular faces, and wherein at least one of the plurality of endplates may have a corresponding, mating dovetail.

9. The apparatus of claim 1, wherein at least one of the first base or the second wedge further comprise a bi-planar wedge.

10. The apparatus of claim 1, wherein the first wedge is disposed at the first threaded post end, and the second threaded post end rotatably engages the second wedge threaded aperture.

11. The apparatus of claim 1, wherein the threaded post is rotatably retained by the first base such that the threaded post can spin within the first wedge without changing the first base longitudinal displacement with respect to the first threaded post end.

12. The apparatus of claim 1, wherein each of the plurality of endplates further comprise an interior angled face configured to rest upon the first wedge and the second wedge.

13. An apparatus, comprising:
   a spinal implant configured to expand in at least two dimensions at the same time, comprising:

a first base connected to a first bi-planar wedge, the first bi-planar wedge having at least one angular wedge face vertically disposed in a first plane, and at least one angular wedge face laterally disposed in a second plane;

a second base statically coupled to the first base;

a second bi-planar wedge slidably disposed between the first base and the second base, the second bi-planar wedge having at least one angular wedge face vertically disposed in a first plane, and at least one angular wedge face laterally disposed in a second plane, wherein the second bi-planar wedge is coupled with the first bi-planar wedge by a threaded post rotatably retained by the first bi-planar wedge and a threaded aperture configured in the second bi-planar wedge; and, a plurality of movable endplates, wherein each endplate of the plurality of endplates has a first end and a second end and is slidably engaged with at least one vertically disposed bi-planar wedge face and at least one laterally disposed bi-planar wedge face;

wherein the plurality of endplates each include one or more linking elements and interior angled faces adapted to slidably engage with the first bi-planar wedge and the second bi-planar wedge, to drive the movable spinal implant endplates radially outward from the longitudinal axis of the threaded post, displacing the second bi-planar wedge and expanding the implant as the threaded post turns; and wherein the linking elements connect the first end of each endplate to the first bi-planar wedge and the second end of each endplate to the second bi-planar wedge to limit the lateral and vertical displacement of each of the plurality of endplates.

14. The apparatus of claim 13, wherein the second bi-planar wedge is slidably engaged with the first bi-planar wedge via a pair of rails laterally extending from the first base and a corresponding pair of rail inserts formed on the second bi-planar wedge.

15. The apparatus of claim 13, wherein the linking element is comprised of fasteners adapted to engage each of the plurality of end plates with each of the first bi-planar wedge and the second bi-planar wedge.

16. The apparatus of claim 13, wherein each of the plurality of endplates is configured with a recess to receive bone graft material.

17. An apparatus, comprising:
a spinal implant configured to expand in at least two dimensions at the same time, comprising:
a first base formed with a first bi-planar wedge on a first side of the first base, the first bi-planar wedge having at least one angular wedge face vertically disposed in a first plane, and at least one angular wedge face laterally disposed in a second plane;

a second base statically coupled to the first base via a pair of rails;

a second bi-planar wedge configured to slide between the first base and the second base along the pair of rails, the second bi-planar wedge having at least one angular wedge face vertically disposed in a first plane, and at least one angular wedge face laterally disposed in a second plane, wherein the second bi-planar wedge is coupled with the first bi-planar wedge by an aligning support and a threaded post rotatably retained by the first bi-planar wedge and a threaded aperture configured in the second bi-planar wedge; and, four movable endplates, wherein each of the four moveable endplates has a first end and a second end and is slidably engaged with at least one vertically disposed bi-planar wedge face and at least one laterally disposed bi-planar wedge face; wherein each of the four moveable endplates each include one or more linking elements and interior angled faces adapted to slidably engage with the first bi-planar wedge and the second bi-planar wedge, to drive the movable spinal implant endplates radially outward from the longitudinal axis of the threaded post, displacing the wedges and expanding the implant both vertically and laterally at the same time as the threaded post turns; and, wherein the linking elements connect the first end of each endplate to the first bi-planar wedge and the second end of each endplate to the second bi-planar wedge to limit the lateral and vertical displacement of each of the plurality of endplates.

18. The apparatus of claim 17, wherein each of the four moveable endplates is configured with a recess to receive bone graft material.

19. The apparatus of claim 17, wherein the apparatus further comprises a locking mechanism configured to prevent the threaded post from turning.

* * * * *